(12) United States Patent
Roberts

(10) Patent No.: US 6,601,451 B1
(45) Date of Patent: Aug. 5, 2003

(54) SYSTEM AND METHOD TO PROVIDE MATERIAL PROPERTY MEASUREMENT USING RE-ENTRANT ULTRASOUND

(75) Inventor: Ronald Allen Roberts, Ames, IA (US)

(73) Assignee: Iowa State University Research Foundation, Ames, IA (US)

( * ) Notice: Subject to any disclaimer, the term of this patent is extended or adjusted under 35 U.S.C. 154(b) by 0 days.

(21) Appl. No.: 09/885,506

(22) Filed: Jun. 20, 2001

(51) Int. Cl.[7] ............................................... G01N 29/16
(52) U.S. Cl. ........................................................ 73/579
(58) Field of Search .......................... 73/579, 597, 598, 73/599, 600, 602, 627–628; 310/313 R, 313 B

(56) References Cited

U.S. PATENT DOCUMENTS

| 3,198,281 A | | 8/1965 | Mifsud | 181/0.5 |
| 3,394,585 A | | 7/1968 | Davey | 73/67.7 |
| 3,741,334 A | | 6/1973 | Kaule | 181/0.5 |
| 3,914,987 A | | 10/1975 | Bickel et al. | 73/67.2 |
| 4,098,131 A | | 7/1978 | Renzel | 73/627 |
| 4,534,223 A | * | 8/1985 | Sinha et al. | 310/313 B |
| 4,758,803 A | * | 7/1988 | Thomas, III | 264/40.1 |
| 4,895,017 A | * | 1/1990 | Pyke et al. | 73/24.06 |
| 5,076,094 A | * | 12/1991 | Frye et al. | 310/313 B |
| 5,214,955 A | * | 6/1993 | Yost et al. | 374/119 |
| 5,627,906 A | * | 5/1997 | Walach | 382/128 |
| 5,698,786 A | * | 12/1997 | Andersen | 73/609 |
| 5,700,952 A | * | 12/1997 | Andersen | 310/313 B |
| 5,859,370 A | | 1/1999 | Suh et al. | 73/627 |

\* cited by examiner

*Primary Examiner*—Helen Kwok
*Assistant Examiner*—Rose M. Miller
(74) *Attorney, Agent, or Firm*—Leydig, Voit & Mayer, Ltd.

(57) ABSTRACT

Presented is a system and method for performing highly sensitive measurement of ultrasonic attenuation in small material volumes. The invention allows the mapping of the variations on the surface of a specimen with a high spatial resolution. An ultrasonic transmitter and receiver transmit an ultrasonic signal through a material volume, receive the transmitted pulse, and then re-transmit the received pulse again through the same material volume. The system establishes an oscillating circuit by establishing a positive feedback loop by connecting the transmitter to the receiver with appropriate gain. This oscillating circuit contains the propagation through the material as a component in the signal path. Such a system and method may be employed to aid in the recovery of stamped or engraved serial numbers that have been removed through machining. Such recovery is useful for law enforcement, particularly in tracing weapons and auto parts that have been involved in a crime.

25 Claims, 5 Drawing Sheets

SYSTEM AND METHOD TO PROVIDE MATERIAL PROPERTY MEASUREMENT USING RE-ENTRANT ULTRASOUND

STATEMENT REGARDING FEDERALLY SPONSORED RESEARCH OR DEVELOPMENT

This invention was developed with government assistance under DOE Contract No. W-7405-Eng-82. The government may have certain rights in this invention.

FIELD OF THE INVENTION

The instant invention relates to systems and methods for performing material property measurements, and more particularly to systems and methods for identifying material property defects through the use of ultrasonic measuring equipment.

BACKGROUND OF THE INVENTION

Most, if not all, consumer and industrial products, equipment, and component parts carry with them some form of serial number or product identification code information. One function of this serial number or product identification information is to individually identify particular products or equipment for warranty and maintenance service tracking. Another function, and with particular classes of consumer and industrial products or component parts possibly a primary function, is to serve as a mechanism to track ownership in case of theft or use in crime.

While many products and component parts include separately affixed identification plates or labels including the serial number or product identification code information, particular classes of products and components have this information stamped or engraved in the product or component part itself. Probably two of the most well known consumer products and component parts that utilize this more permanent technique of stamping or engraving product serial number information thereon are firearms and some automotive parts, e.g. engine blocks. As with other products and components parts, these stamped or engraved serial numbers serve to identify and allow the tracking of proper ownership in case of theft, or use in a crime. However, many criminals have recognized that the serial number information may well provide the authorities the very information that would lead to their arrest, and so have engaged in the removal of the serial number information. Often times the criminals simply machine off the stamped or engraved serial number.

Unfortunately, with current technology the tracking of proper ownership of these products and component parts once the serial number has been machined off, absent other evidence, has proven to be extremely difficult for law enforcement officials. Since many criminals routinely engage in the removal of stamped or engraved serial number information from auto parts and fire arms in attempt to conceal their or the rightful owner's identity, there exists an urgent need for new technology that enables the recovery of this machined-away serial number information.

The ability to extract serial number information from products and components that have been subject to or used in a crime would greatly enhance law enforcement's ability to apprehend criminals and return property to its rightful owner. The stamping and engraving processes used to place the serial number on the product or component not only results in a visually perceptible impression on the surface of the product or component, but it also introduces a distortion in the microstructure of the material itself well below the surface indentation. As recognized by the inventor of the instant application, the micro-structural distortion is localized to the serial number impression and remains even after the visually perceptible surface indentation has been removed through a machining operation. Unfortunately, since this micro-distortion is localized to the small material volume of the serial number impression, conventional ultrasonic techniques of detecting variations in a material volume are unable to detect and map these distortions.

Measurements of acoustic velocity and attenuation are used in various applications to detect changes in material properties. For example, uniformity in metal microstructure can be sensed by monitoring uniformity in acoustic velocity and attenuation. Such measurements have traditionally been performed using ultrasonic signal propagation paths with lengths measured in tens or hundreds of wavelengths. This is due to the fact that the ability to detect a subtle difference in acoustic velocity or attenuation increases directly with the length of material through which the signal propagates. Such a measurement could be used, for example, to determine uniformity in material processing from one batch of material to the next by comparing differences in measured acoustic properties in representative samples, each being several inches in length.

Such measurements may be performed using instrumentation configured as indicated in FIG. 13. In such a configuration, an ultrasonic pulse is transmitted through a specimen 21 several inches long by placing two ultrasonic transducers 23, 25 on either end of the specimen 21, one 23 to transmit and the other 25 to receive. Typical transducers might be 0.5 inch in diameter, and be design to transmit broadband ultrasonic signals with a 5 MHz center frequency. Ultrasonic wavelengths typically range from 0.1 to 1.0 mm.

An obvious drawback of the measurement technique illustrated in FIG. 13 is the inability to detect localized differences in material properties within the sample volume. That is, the system of FIG. 13 has poor spatial resolution. One technique that does allow the detection of localized variations in material acoustic properties is scanning acoustic microscopy. This technique is similar in approach to that shown in FIG. 13 except that it does not use transmitting 23 and receiving 25 transducers on opposite end of a specimen 21. Instead, a pair of focused transducers 27, 29 are used to propagate a surface wave a short distance over the surface of a specimen 21 as illustrated in FIG. 14.

A surface wave is a special type of wave in a solid material that clings to the surface, as opposed to penetrating through the solid. As illustrated in this FIG. 14, a surface wave can be generated by launching a pulse through water toward the surface at a specific critical angle, slightly greater than the critical angle for total wave reflection. When the pulse hits the surface, it will generate a surface wave pulse within the solid. As the surface wave propagates over the surface, it radiates energy back into the water. By using a pair of focused transducers, one 27 to generate a surface wave pulse at some position and a second 29 to detect the pulse radiated back into the water a short distance away from the generation point, a signal path can be established that includes a small volume of solid material.

The surface wave path L can be adjusted in length from a fraction of a wavelength to a few wavelengths. Acoustic attenuation and velocity in the solid material can be determined by monitoring received signal transit times and amplitudes. By mechanically scanning the transducer pair over the specimen surface, an image can be formed of material properties throughout a thin layer near the specimen surface, with a relatively high spatial resolution. The drawback of the scanning acoustic microscopy measurement depicted in FIG. 14 is that, while measurements can be made with high spatial resolution (e.g. a fraction of a wavelength), measurement sensitivity to variation in material properties suffers because of the relatively short propagation path L in the solid material. As such, small residual material distortions remaining after a serial number has been machined off a component cannot be reliably recovered. A need exists, therefore, for a measurement system and method that has high sensitivity to material properties, as with the measurement system of FIG. 13, yet at the same time has high spatial resolution, as with the measurement system of FIG. 14.

SUMMARY OF THE INVENTION

It is therefore an object of the instant invention to overcome these and other problems existing in the art. More specifically, it is an object of the instant invention to provide a system an a method to aid in the recovery of serial number or other identification information from consumer or industrial products and component parts that have had this information machined away. It is a further object of the invention to provide a system and method to detect small, local residual material variations in the product or component originally resulting from the serial number stamping or engraving process. Additionally and more generally, it is an object of the instant invention to provide a system and method for the measurement of material properties in small volumes of the material. It is a still further object of the invention to obtain this measurement with conventional laboratory-grade measurement instruments.

In view of these and other objects of the invention, it is a feature of the invention to provide a system and method to perform highly sensitive measurement of localized ultrasonic attenuation and velocity in small material volumes. It is a further feature of the invention to allow a mapping of the variation of these ultrasonic properties on the surface of the product, component, or other specimen with a high spatial resolution. Additionally, it is a feature of the invention to provide such high spatial resolution of the measurement in material volumes on the order of a wavelength in length.

In view of these objects and features, the system and method of the invention perform high-sensitivity acoustic property measurements in small material volumes. As will be discussed more fully below, in conventional ultrasound measurements a tradeoff is maintained between spatial resolution (the size of the measured material volume) and the measurement sensitivity (the smallest detectable difference in velocity and/or attenuation through the material). In the instant invention, a technique has been devised for circumventing this tradeoff by artificially "enlarging" the effective size of the test material volume by repeatedly transmitting the acoustic signal through same small material volume. Through this new technique, measurements can be performed on material volumes on the order of a wavelength in length that have sensitivity comparable to conventional measurements requiring volumes measured in hundreds or thousands of wavelengths. This allows for the identification of localized, residual material defects as may have been caused by the original stamping or engraving process.

In accordance with an embodiment of the invention, this increased sensitivity is attained in such a small material volume by establishing an oscillating ultrasonic circuit in which the material being measured forms a component in the electro-acoustic oscillator. In this way, the sensitivity of the measurement is no longer controlled by the physical extent of the material volume under test, but rather by the length of time over which the oscillation is monitored. The technique and apparatus for performing such measurement in accordance with the instant invention utilizes a technique similar to scanning acoustic microscopy. However while scanning acoustic microscopy provides high spatial resolution, the measurement sensitivity to variations in the material properties itself suffers because of the relatively short propagation path in the solid material. To gain increased measurement sensitivity to variations in the material, the concept of signal re-transmission is employed. That is, a signal is repeatedly sent through the same small volume of length of the material so that the effects of the material acoustic attenuation and velocity would accumulate as if the signal were propagating through several inches of that material.

A simple means of re-transmitting the received signal in accordance with one embodiment is to apply an amplified version of the output signal from the receiver to the transmitter input. In practice, this circuit results in the establishment of an oscillating circuit. The frequency of this oscillation is determined by (a) the transmit time from the transmitter to the receiver, and hence the acoustic velocity of the solid material, and (b) the system center frequency of the transmit/receive transducers and electronics. In this invention an oscilloscope is used to monitor the oscillation frequency, which, as the signal transmission is repeated N times, will be dominated by a single frequency. Since the frequency of oscillation is dependent upon the acoustic velocity of the solid material, any monitored variation of the frequency of oscillation over time corresponds to a variation in the acoustic velocity of the material itself. In this way, small variations in acoustic velocity of the material may be monitored by utilizing a conventional laboratory-grade oscilloscope display.

Through such a system and method, an embodiment of the instant invention may be employed to recover stamped or engraved serial numbers that have been removed through machining by making sensitive measurements of localized variations in material ultrasonic properties on the specimen surface. These small, residual variations are a result of the stamping or engraving process, and may be detected even after the serial number has been machined away. Such recovery of serial number information is useful for law enforcement, particularly in tracing firearms and weapons that have been involved in a crime. Further, such recovered serial number information may aid in the identification and tracing of auto parts that have been removed from a stolen vehicle.

Other objects and advantages of the invention will become more apparent from the following detailed description when taken in conjunction with the accompanying drawings.

Figure 1:
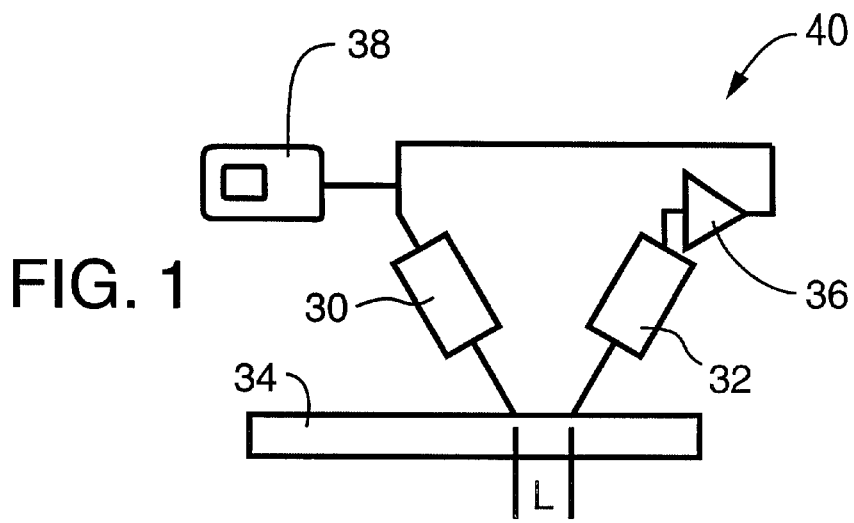
FIG. 1 is a block diagramatic illustration of an embodiment of an oscillating ultrasonic measurement circuit constructed in accordance with the teachings of the invention.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE PREFERRED EMBODIMENTS

The instant invention presents a system and method for performing high-sensitivity acoustic property measurements in small material volumes. As discussed above, a trade-off is maintained in conventional ultrasound measurements between spatial resolution (size of measured material volume) and measurement sensitivity (the smallest detectable difference in velocity and/or attenuation). In the instant invention, a technique has been devised for circumventing this trade-off by artificially "enlarging" the size of the test material volume by repetitively re-transmitting the acoustic signal through the same small material volume. Using this technique, measurements can be performed in volumes on the order of a wavelength in extent that have sensitivity comparable to conventional measurements requiring volumes measured in hundreds or thousands of wavelengths.

The system and method of the invention attain this sensitivity by establishing an oscillating ultrasonic circuit in which the material being measured forms a component of the electro-acoustic oscillator. In this system, the sensitivity of the measurement is no longer controlled by the physical extent of the material volume under test as with prior systems. Rather, the sensitivity of the measurement is controlled by the length of time over which the oscillation is monitored. The ultimate sensitivity is therefore determined by the stability of the electronic clock used in the monitoring instrumentation and the mechanical stability of the experimental fixturing. As technologies readily exist for extremely accurate control of these parameters, the instant invention presents a significant potential for a new generation of high-sensitivity acoustic sensors.

While typical scanning acoustic microscopy is known to provide an image of the material properties throughout a thin layer near a specimen's surface with a relatively high spatial resolution, this conventional technique has a low sensitivity to variations in material properties because of the relatively short propagation path of the generated surface acoustic wave in the solid material. To overcome this deficiency in conventional surface acoustic microscopy, the instant invention utilizes the concept of signal re-transmission of the received acoustic wave at the end of the transmission length.

As recognized by the inventor of the instant invention, if a signal could be repeatedly sent through the same small volume of length L, the effects of material acoustic attenuation and velocity would accumulate as if the signal were propagating through several inches of material. One approach to doing this is to transmit a pulse, record the received pulse, then play back the received pulse into the transmitter. By repeating this process N times, the effective length of the transmission path would be increased to N times L. Physical implementation of such a procedure, however, requires extremely precise data recording and playback equipment, so as to capture and retain very minute changes in the signal. Furthermore, truly simulating signal propagation through a longer solid path length would require transducers with nearly ideal band-pass characteristics. Indeed, if such equipment were available, there would be no need to re-transmit the signal because the required sensitivity to the material properties would be present in the first transmitted signal. Nevertheless, this embodiment serves to explain the functioning of a much simpler experimental procedure.

In an alternate embodiment of the instant invention, a simple method of re-transmitting the received signal applies an amplified version of the output signal from the receiver to the transmitter input. This embodiment is illustrated in FIG. 1 to which specific attention is now directed. As may be seen, an ultrasonic transmitter 30 and receiver 32 are positioned to establish a surface acoustic wave on a specimen 34 over a small material volume of length L. The output of the receiver 32 is coupled through an amplifier 36 to the input of the transmitter 30. A typical laboratory-grade oscilloscope 38 is then used to monitor this input signal.

The circuit configuration of this embodiment results in the establishment of an oscillating circuit 40 that includes a length L of the specimen as part of the circuit. The frequency of the circuit's oscillation is determined by two factors: 1) the transit time from the transmitter to the receiver, and hence the acoustic velocity of the solid material; and 2) the system center frequency of the transmit 30 and receive 32 transducers and associated electronics. For sustained oscillation, the signal transit time must be an integer multiple of the period of oscillation. This implies that the oscillation frequency must be an integer multiple of the fundamental oscillation frequency (reciprocal of the signal transit time). As will be recognized by those skilled in the art, this requirement places a constraint on possible oscillation frequencies of the system. Among these possible frequencies, the actual oscillation frequency that is realized is determined by the band pass characteristics of the transducers and associated electronics.

Figure 2:
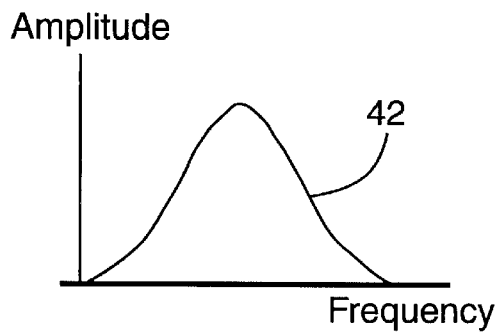
FIG. 2 is a graphical illustration of an ultrasonic system frequency band-pass plot.
Figure 3:
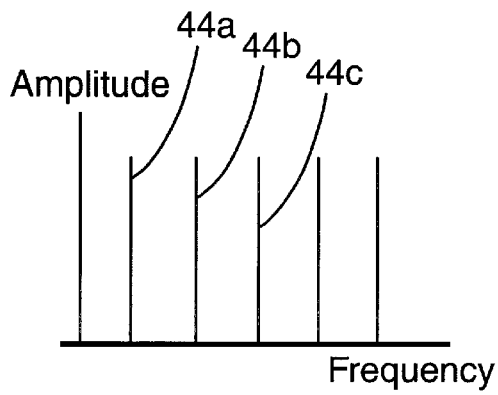
FIG. 3 is a graphical illustration of discreet oscillation frequencies for the system of FIG. 1.

In analyzing the system effect of these constraints on the system of FIG. 1, it is noted that the typical ultrasonic system frequency band-pass has an amplitude characteristic 42 as illustrated in FIG. 2. It is further noted that the above-described constraint on possible oscillation frequencies dictates that the oscillation signal can only exist at discrete frequencies 44a, 44b, 44c, etc., as indicated by FIG. 3. Now, if a signal having the spectrum of FIG. 3 were transmitted one time through the ultrasonic system 40 having a band-pass characteristic as illustrated in FIG. 2, according to elementary system theory the system output would be the product of the spectra of FIGS. 2 and 3. This result is illustrated in FIG. 4.

Figure 4:
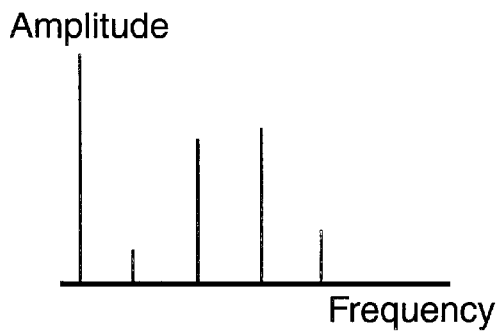
FIG. 4 is a graphical illustration of the effect on the discreet oscillation frequencies of the system of FIG. 1 illustrated in FIG. 3 after transmission through the system having the band-pass of FIG. 2.
Figure 5:
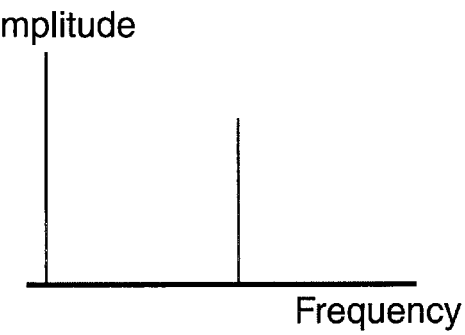
FIG. 5 is a graphical illustration of the oscillation frequency resulting from the repeated transmission of the received waveform of FIG. 4 N times.

Now, if the waveform of FIG. 4 were transmitted (sent back) through the system 40 having the band-pass characteristic of FIG. 2, the output signal following this re-transmission would be the product of FIGS. 2 and 4. If this re-transmission were repeated N times, the output signal would be FIG. 2 multiplied by FIG. 4 N times. It is evident therefore that as N becomes large, the spectrum of the oscillating signal will be dominated by the frequency spike illustrated in FIG. 4 having the largest amplitude, as illustrated in FIG. 5. Thus the frequency of oscillation will correspond to the largest spike in the spectra of FIG. 4.

The preceding discussion considers the relative magnitude of the frequency spikes in the spectral response, but gives no consideration to actual spike amplitudes. As will be recognized by one skilled in the art, under linear system theory amplitude will grow without bound if the largest spike in FIG. 4 has an amplitude greater than unity. In a preferred embodiment, therefore, this amplitude will be limited by non-linear response characteristics of the system electronics. Using a simplistic view of non-linear system behavior, the output amplitude of an amplifier varies as a function of the input amplitude according to a plot such as that of FIG. 6.

Figure 6:
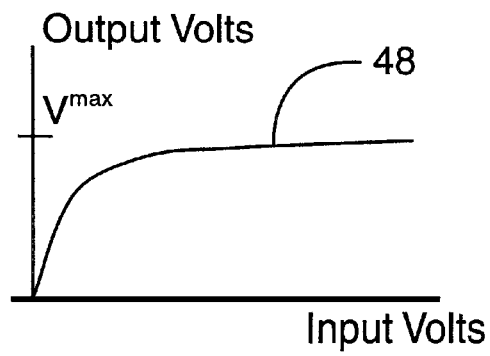
FIG. 6 is a graphical illustration of the output characteristics of an amplifier versus its input.
Figure 7:
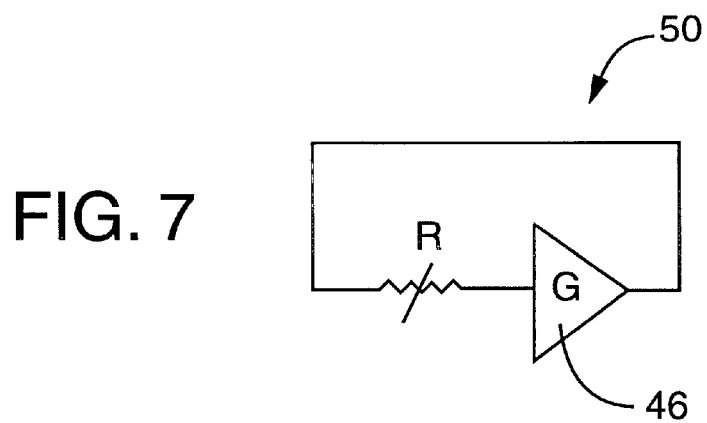
FIG. 7 is a simplified schematic illustration of an oscillating circuit to aid in the understanding of the invention.

When an amplifier 46 is used as an oscillating circuit 50 by connecting its output to its input as shown in FIG. 7, the amplifier output will stabilize at the oscillating voltage for which the voltage drop across the attenuator R equals the voltage gain G provided by the amplifier 46. Therefore, the point on the curve 48 of FIG. 6 at which the oscillator 50 stabilizes can be selected by adjusting the attenuation R. While this is a simplification of the physical phenomena involved in the oscillating circuit, it serves to explain an observed non-linear dependence of signal amplitude on circuit attenuation. In the ultrasonic system configuration of FIG. 1, it is noted that, in addition to attenuation provided by electronic instrumentation, attenuation is introduced by transducer transduction efficiencies and material acoustic attenuation.

Figure 14:
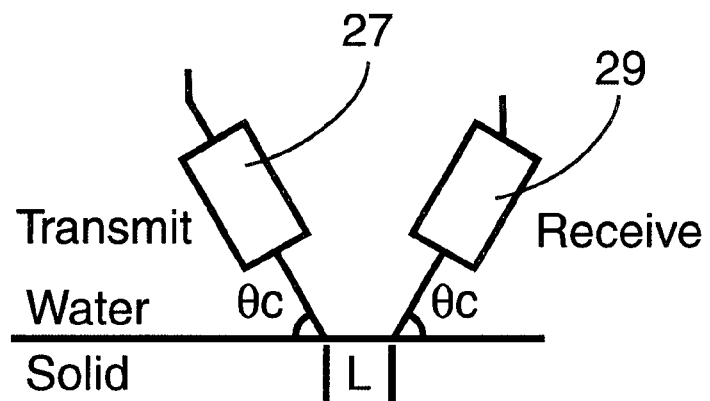
FIG. 14 is a simplified block diagrammatic illustration of a prior method of performing scanning acoustic microscopy measurement.

In the preceding discussion of FIG. 14, it was described how the oscillating frequency of the ultrasonic circuit is determined by the signal transit time from the transmitting 27 to receiving 29 transducers, and how the transit time is in turn determined by the acoustic velocity over the propagation path L. It follows, therefore, that the net effect of a small change in acoustic velocity is to slightly shift the horizontal position of the frequency spike in FIG. 5, that is, to slightly shift the oscillating frequency of the oscillator. Consequently, detection of an acoustic velocity variation reduces to detection of a small change in oscillating frequency. This is a task that can be performed to a very high precision using modest instrumentation, e.g. a standard laboratory digital oscilloscope.

Figure 8:
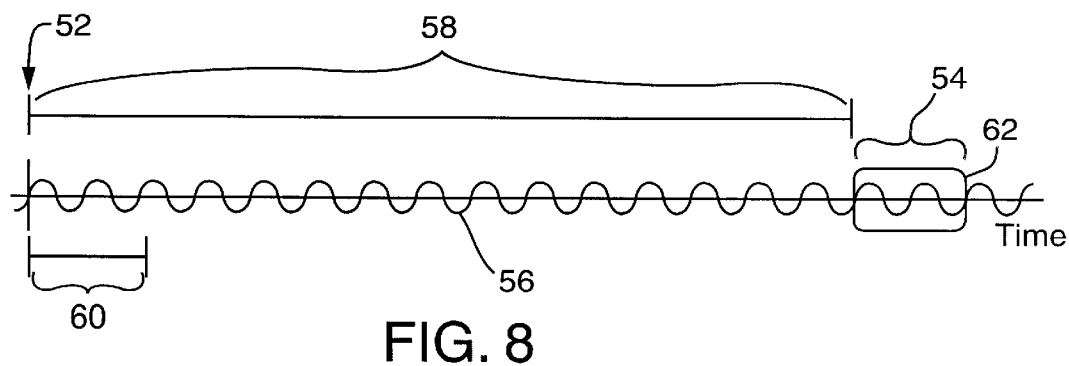
FIG. 8 graphically illustrates a relationship between transmission time and trigger time in accordance with one embodiment of the invention.
Figure 9:
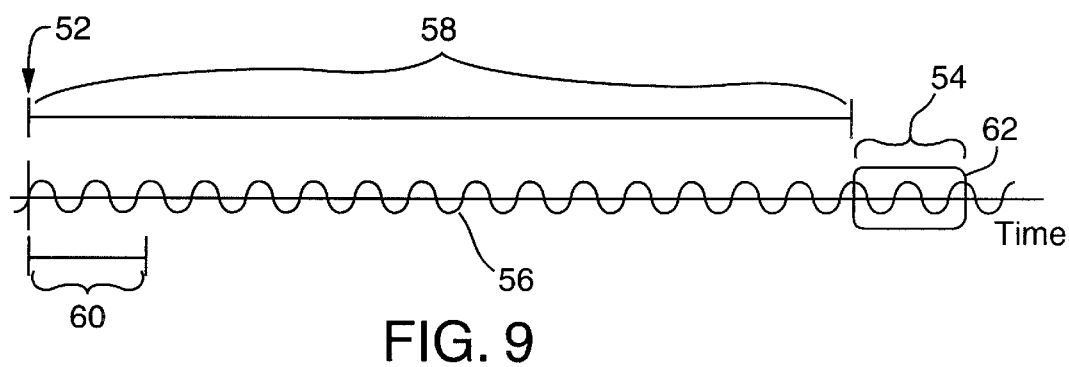
FIG. 9 graphically illustrates a relationship between transmission time and trigger time in accordance with one embodiment of the invention wherein a difference in acoustic velocity is detected from that of FIG. 8.
Figure 10:
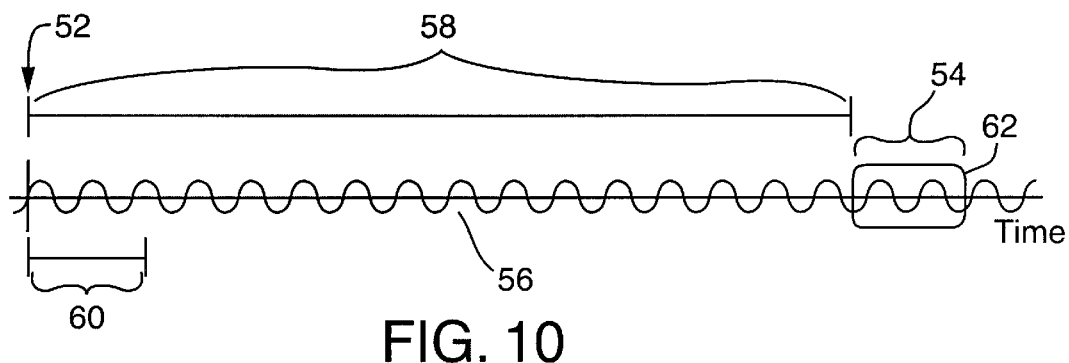
FIG. 10 graphically illustrates a relationship between transmission time and trigger time in accordance with one embodiment of the invention wherein a difference in acoustic velocity is detected from that of FIGS. 8 and 9.

To conduct such a measurement in accordance with one embodiment of the instant invention, an oscilloscope 38 is triggered at some arbitrary time 52 by the oscillating circuit output voltage 56. As illustrated in FIG. 8, once the oscilloscope has been triggered at point 52, a small segment 54 of the output voltage 56 is recorded on the oscilloscope display 62 at a later time as determined by the oscilloscope trigger delay 58. This trigger delay 58 is: preferably longer than the transit time 60 through the specimen. Small changes in oscillating frequency resulting from material property changes will manifest themselves in the recorded signal segment 54 as a shift to the left (for decreased time) on the oscilloscope display 62 as illustrated in FIG. 9, or as a shift to the right (for increased time) on the oscilloscope display 62 as illustrated in FIG. 10. A shift to the left as illustrated in FIG. 9 indicates a shortening in the period of oscillation, corresponding to a decrease in signal transit time, and hence an increase in acoustic velocity. The converse is true for a signal shift to the right on the oscilloscope display as illustrated in FIG. 10.

Sensitivity to changes in oscillating frequency, and hence acoustic velocity, are proportional to the length of the trigger delay 58. A trigger delay equal to the signal transit time 60 will yield a sensitivity to velocity comparable to the simple "one time through" transmission measurement illustrated in FIG. 14. By increasing the trigger delay 58 to some multiple N of the signal transit time 60, a sensitivity comparable to a transmission path N time longer than the actual transmission path is obtained. In this way, the small material volume is virtually enlarged to achieve the high spatial resolution with the high sensitivity to material properties unavailable with the system of FIG. 14.

To demonstrate the level of sensitivity achievable, experiments were performed using the oscillating ultrasonic circuit of the embodiment illustrated in FIG. 1. In this exemplary system, a pair of 0.75 inch diameter, 1.0 inch focal length, 10 MHz center frequency transducers were used. The transducers were oriented for surface wave generation in metal (nickel alloy) using a 0.8 mm long surface wave path L. A first experiment demonstrated the enhanced sensitivity of the system to changes in acoustic velocity. To introduce a small change in acoustic velocity, a temperature variation was introduced into the acoustic medium. This was achieved by first placing an ice chip into the water immersion bath in which the experiment was performed. Next, the temperature variation was achieved by placing the hot tip of a soldering pencil into the water.

Using a trigger delay equal to the transit time between transmitter and receiver (0.034 milliseconds), the variation in acoustic velocity was completely undetectable using a standard laboratory grade oscilloscope. This result duplicates the sensitivity of conventional acoustic microscopy measurements achievable from the system illustrated in FIG. 14. The trigger delay 58 was then increased to 34 milliseconds. Using this trigger delay, the velocity shifts introduced by the temperature variation were easily detectable, observed as phase shifts in the recorded signals on the order of several tens of periods. A simple calculation indicates that, at a trigger delay of 34 milliseconds, a phase shift of one period at 10 MHz indicates a change in velocity of ~0.0003 percent. This is several orders of magnitude more sensitive than typical through-transmission ultrasonic measurements.

It was found that a limit to the sensitivity of the measurement is determined by the stability of the time base in the digital oscilloscope. When time delays significantly greater than 34 milliseconds were attempted, jitter in the recorded signal became unacceptably large, precluding a reliable measurement. Therefore, it is noted that yet greater sensitivities are obtainable through use of more stable timing electronics. An additional factor impacting sensitivity is mechanical stability of the experimental fixturing. It was observed that the measurement became quite sensitive to room vibrations, due to sources such as air circulation equipment. Such factors are routinely compensated for in optical experiments. It is therefore evident that the experiments discussed here of one exemplary embodiment are not nearly representing the ultimate sensitivity of the measurement system and method of the invention. Therefore, this discussion should be taken by way of example, and not by way of limitation.

The foregoing discussion assumes that a single spectral spike is clearly larger than the others and hence unambiguously dominates the oscillator response (see FIGS. 4 and 5). However, it may be possible for two neighboring spectral spikes of nearly equal amplitude compete for dominance in the oscillator response. Such a situation may be observed as random jumping of signal phase observed at long time delays. However, such phase instability cannot exist at time intervals corresponding to exact integer multiples of the fundamental signal transit time. Even though the oscillation center frequency may be randomly jumping from one spectral line to another, the phase at the integer multiple of the transit time must remain stable due to the fundamental condition for establishing a sustained oscillation. Thus, even when mode jumping is occurring, time delays can always be found at which the phase is stable.

To exploit this fact, an alternate embodiment of the instant invention provides a method, which may be implemented as a computer algorithm, that locates and tracks such a point of stability nearest to the selected oscilloscope trigger delay. Once this point of stability is determined, the movement in time position of this point of stability is used to calculate the variation in acoustic velocity. In this way, the variations in material properties may be detected with the same spatial resolution and high sensitivity as for situations that are dominated by only a single spectral spike.

Figure 11:
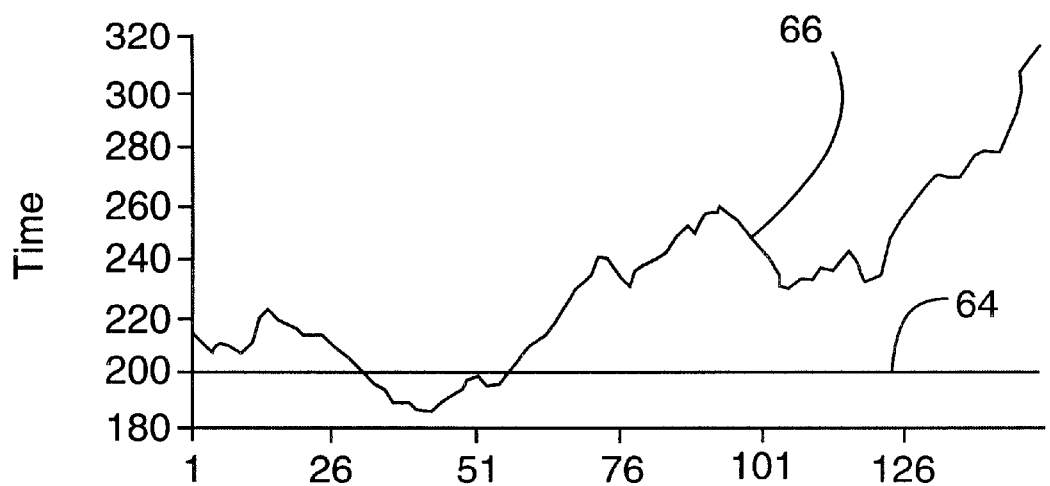
FIG. 11 is a graphical illustration of the time position of a signal peak in the oscilloscope display as a function of probe position comparing the sensitivity and spatial resolution of an embodiment of the instant invention to that achievable by conventional through-transmission techniques.
Figure 13:
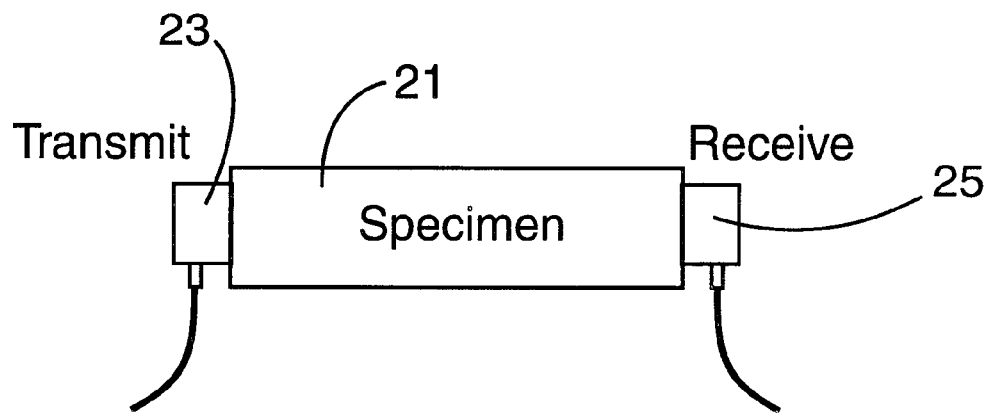
FIG. 13 is a simplified block diagrammatic illustration of a prior measurement technique to sense non-uniformity in acoustic velocity and attenuation in a metal microstructure.

As a demonstration of the detection of surface wave velocity variation using an embodiment of the ultrasonic oscillating circuit of FIG. 1, the 10 MHz transducer pair 30, 32 was scanned on a line over the surface of a fused quartz specimen. Fused quartz was selected because it has an extremely uniform internal structure, and hence has a spatially uniform surface wave velocity. FIG. 11 plots the time position of a signal peak in the oscilloscope display as a function of probe position over 0.75 mm. The vertical units of the plot represent 2.5 nanosecond time steps. The horizontal units represent 0.005 mm spatial steps. Results are compared for a 0.034 millisecond trigger delay by trace 64 and a 3.4 millisecond trigger delay by trace 66. The 0.034 millisecond delay corresponds to one trip through the acoustic path, and hence represents the measurement sensitivity of a conventional through-transmission experiment (see FIG. 13).

The 0.034 millisecond data is seen to be a straight horizontal line 64, indicating that the measurement detects no variation in transit time, and hence no variation in acoustic velocity. The 3.4 millisecond data illustrated by trace 66 displays a substantial variation in transit time. The 3.4 millisecond delay represents a one hundred-fold increase in the effective acoustic path length. The resulting increase in detection sensitivity is clearly evident in the plot of FIG. 11.

As will be recognized by one skilled in the art, the velocity measurement described above for one embodiment of the invention uses signal transit time to sense velocity changes. In an alternate embodiment of the invention, the amplitude of the oscillating ultrasonic circuit is used to provide a very sensitive means to detect spatial variations in acoustic attenuation. In the discussion of FIGS. 6 and 7, it was noted that the amplitude of the oscillating signal can be controlled by adjusting the attenuation in the circuit. When the oscillating amplitude is small, the oscillating circuit displays a high sensitivity to changes in attenuation. To see this mathematically, consider the plot of FIG. 6 when the input voltage is small. For a sufficiently small voltage, the output voltage can be approximated as follows:

$$V_{out} = A \cdot V_{in} - \epsilon V_{in}^2$$

In this equation, A is the linear gain coefficient, representing the combined contributions of attenuation R and gain G in FIG. 7. The non-linear coefficient $\epsilon$ will be quite small in a quality amplifier. To establish a small amplitude oscillation, the gain A should be slightly greater than unity. That is, $A = 1 + \delta$, where $\delta$ is small. Requiring that $V_{out} = V_{in}$, it is seen that $V_{out} = V_{in} = \delta/\epsilon$. The sensitivity to attenuation is indicated by the derivative of this voltage with respect to gain, seen to be $dV/d\delta = 1/\epsilon$. Thus, as the oscillation amplitude is reduced by decreasing gain, the sensitivity to changes in gain approaches the reciprocal of the leading order non-linear gain coefficient. As this coefficient is engineered to be as small as possible, an extremely high sensitivity results. In one embodiment, a 1 percent variation in attenuation is observed to produce a 200 percent change in signal amplitude, representing a gain of 46 dB in sensitivity over a conventional through-transmission ultrasonic circuit.

Figure 12:
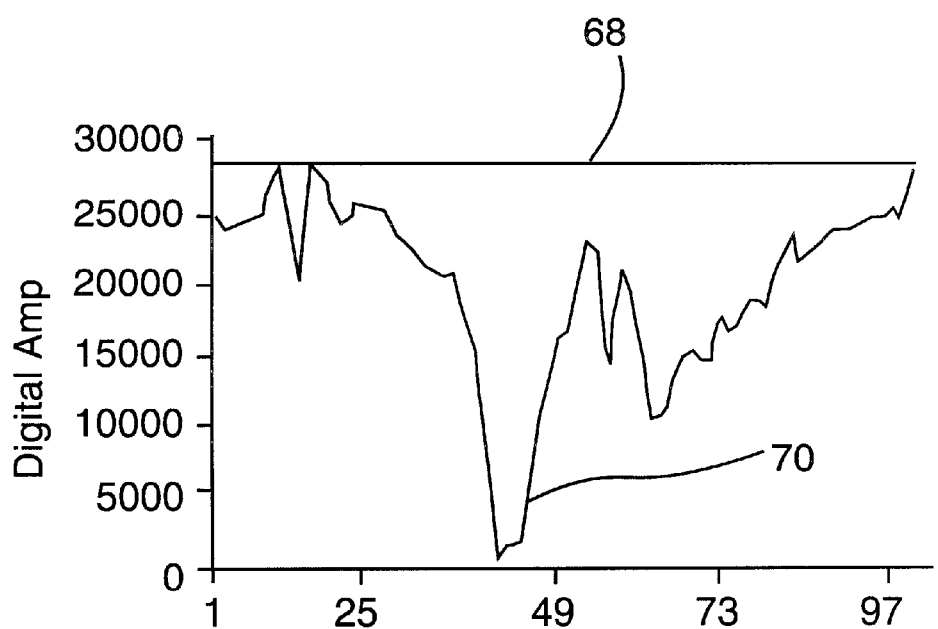
FIG. 12 is a graphical illustration of the amplitude variation of a signal peak in the oscilloscope display as a function of probe position comparing the sensitivity and spatial resolution of an alternate embodiment of the instant invention to that achievable by conventional through-transmission techniques.

To demonstrate the amplitude sensitivity of the measurement of this embodiment of the invention, a line scan was performed on a quartz specimen such as that used in FIG. 11, but now with the objective of monitoring amplitude variation. The result of this scan is shown in FIG. 12. Data was collected using both the oscillating ultrasonic circuit measurement in accordance with the instant invention, and a conventional pulsed through transmission measurement that transmits the signal once through the specimen. A scan was performed over 1.0 mm. The unit of the horizontal axis of FIG. 12 represents a 0.01 mm step. The unit of the vertical axis represents a 15 bit digital recording of amplitude.

As may be observed from FIG. 12, the conventional through transmission measurement illustrated by trace 68 displays almost no amplitude variation over the 1 mm scan. The greater sensitivity of this embodiment of the oscillating circuit of the invention to attenuation in the acoustic signal path illustrated by trace 70 is evident.

Numerous modifications and alternative embodiments of the invention will be apparent to those skilled in the art in view of the foregoing description. Accordingly, this description is to be construed as illustrative only and is for the purpose of teaching those skilled in the art the best mode for carrying out the invention. Details of the structure and implementation of the various components described above can be varied substantially without departing from the spirit of the invention, and exclusive use of all modifications that come within the scope of the appended claims is reserved.

What is claimed is:

1. A method of measuring variations in material properties in a specimen at different locations, comprising the steps of:

A) transmitting an acoustic signal to establish an acoustic wave on a surface of the specimen over a material volume of length L at a first location of the specimen;

B) receiving the acoustic signal at the end of the length L;

C) amplifying the acoustic signal received in step B);

D) repeating steps A) through C) N times, where N is greater than 1, with the acoustic signal amplified in step C) to establish an oscillating acoustic circuit including as a component thereof the material volume of length L; and E) repeating steps A) through D) at a second location of the specimen.

2. The method of claim 1, wherein step D) is performed to establish the oscillating acoustic circuit such that a frequency of oscillation is established at an integer multiple of a fundamental oscillation frequency.

3. The method of claim 1, further comprising the step of F) monitoring the acoustic signal in the oscillating acoustic circuit over a period of time exceeding a transit time of the acoustic wave over the length L.

4. The method of claim 3, wherein step F) further comprises the steps of:

G) setting a trigger delay for an oscilloscope for a period exceeding the transit time;

H) starting the trigger delay at a point on the acoustic signal;

I) capturing the acoustic signal upon the expiration of the trigger delay; and

J) determining a material property change by observing a phase shift in the acoustic signal captured in step I.

5. The method of claim 4, wherein step G) comprises the step of K) setting the trigger delay at an integer multiple of the transit time.

6. The method of claim 4, further comprising the steps of:

L) determining a point of phase stability nearest the trigger delay;

M) monitoring a time position of the point of phase stability; and

N) determining a material property change by observing a movement in the time position of the point of phase stability.

7. The method of claim 3, wherein step F) further comprises the steps of:

G) setting a trigger delay for an oscilloscope for a period exceeding the transit time;

H) starting the trigger delay at a point on the acoustic signal;

I) capturing the acoustic signal upon the expiration of the trigger delay; and

J) determining a material property change by observing an amplitude variation of the acoustic signal.

8. The method of claim 1, wherein step A) comprises the step of transmitting an ultrasonic signal.

9. A method of measuring variations in material properties in a specimen, comprising the steps of:

A) transmitting an acoustic signal to establish an acoustic wave on a surface of the specimen over a material volume of length L;

B) receiving the acoustic signal at the end of the length L;

C) amplifying the acoustic signal received in step B); and

D) repeating steps A) through C) N times, where N is greater than 1, with the acoustic signal amplified in step C) to establish an oscillating acoustic circuit including as a component thereof the material volume of length L;

E) repeating steps A) through D) at different locations on the specimen; and

F) mapping material property variations at the different locations on the specimen.

10. A method of measuring variations in material properties in a specimen, comprising the steps of:

A) transmitting an acoustic signal to establish an acoustic wave on a surface of the specimen over a material volume of length L;

B) receiving the acoustic signal at the end of the length L;

C) amplifying the acoustic signal received in step B); and

D) repeating steps A) through C) N times, where N is greater than 1, with the acoustic signal amplified in step C) to establish an oscillating acoustic circuit including as a component thereof the material volume of length L; and wherein the length L is approximately one wavelength of the acoustic signal in extent.

11. A method of recovering stamped and engraved serial number information from a specimen that has had the serial number information removed therefrom by machining, comprising the steps of:

A) positioning a pair of ultrasonic transducers at a location over the specimen from which the serial number information has been removed;

B) transmitting an acoustic signal from one of the ultrasonic transducers to establish an acoustic wave on a surface of the specimen;

C) receiving the acoustic signal by the other of the ultrasonic transducers;

D) re-transmitting the acoustic signal received by the other of the ultrasonic transducers to establish an oscillating circuit, the oscillating circuit including as a component thereof the specimen;

E) monitoring the acoustic signal at a time exceeding the transit time of the acoustic signal from one transducer to the other transducer to determine a material property at the location;

F) moving the pair of ultrasonic transducers to a different location of the specimen;

G) repeating steps B) through F) to establish a mapping of material properties at the different locations of the specimen from which the serial number information has been removed.

12. The method of claim 11, wherein step A) is performed such that the acoustic wave on the surface of the specimen established by step B) travels over a length L of the specimen, the length L being on the order of one wavelength of the acoustic signal in extent.

13. The method of claim 11, wherein step B) comprises transmitting an acoustic signal from one of the ultrasonic transducers to establish an acoustic wave on a surface of the specimen.

14. The method of claim 11, wherein step E) comprises the step of monitoring a phase relationship of the acoustic signal.

15. The method of claim 11, wherein step E) comprises the step of monitoring a time position of a point of phase stability in the acoustic signal.

16. The method of claim 11, wherein step E) comprises the step of monitoring an amplitude of the acoustic signal.

17. The method of claim 11, wherein step E) further comprises the step of extending the time at which the acoustic signal is monitored to increase a sensitivity to minute material property changes in the specimen.

18. The method of claim 11, further comprising the step of amplifying the acoustic signal received by step C) prior to the re-transmitting step D).

19. An electro-acoustic oscillator for providing high-sensitivity acoustic property measurements with high spatial resolution within a small material volume of a specimen at various locations of the specimen, comprising:

a pair of transducers positioned in relation to one another such that an acoustic signal transmitted by one transducer and establishing a surface acoustic wave in the small material volume of the specimen is received by the other transducer, the pair of transducers being movable in relation to the specimen;

an amplifier having an input coupled to an output of the transducer that is positioned to receive the acoustic signal, and an output coupled to an input of the transducer that is positioned to transmit the acoustic signal; and acoustic signal monitoring equipment coupled between the pair of transducers, the acoustic signal monitoring equipment operable to monitor the acoustic signal for a period longer than a transit time of the acoustic signal through the specimen; and wherein the pair of transducers and the amplifier are operable to establish an oscillating acoustic circuit having as a component thereof the specimen, the one transducer re-transmitting the acoustic signal received by the other transducer N times, wherein N is greater than 1.

20. The oscillator of claim 19, wherein the one transducer is operable to transmit an ultrasonic signal.

21. The oscillator of claim 19, wherein the acoustic signal monitoring equipment is an oscilloscope.

22. The oscillator of claim 21, wherein the oscilloscope has a trigger delay set longer than the transit time of the acoustic signal, the oscilloscope capturing the acoustic signal upon expiration of the trigger delay.

23. The oscillator of claim 22, wherein sensitivity to material properties is increased by increasing by lengthening the trigger delay.

24. The oscillator of claim 22, wherein a change in material properties is detectable as a phase shift in the acoustic signal captured by the oscilloscope.

25. The oscillator of claim 22, wherein a change in material properties is detectable as an amplitude variation in the acoustic signal captured by the oscilloscope.

* * * * *